(12) United States Patent
Ikeda et al.

(10) Patent No.: US 6,617,429 B1
(45) Date of Patent: Sep. 9, 2003

(54) APOPTOSIS INHIBITORY PROTEIN, GENE ENCODING THE PROTEIN AND CDNA THEREOF

(75) Inventors: Joh-E Ikeda, Tokyo (JP); Kenji Yamamoto, Kanagawa (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/705,872

(22) Filed: Nov. 6, 2000

Related U.S. Application Data

(63) Continuation-in-part of application No. 09/239,797, filed on Jan. 29, 1999, now abandoned.

(51) Int. Cl.[7] .............................................. C07K 14/00
(52) U.S. Cl. ..................................................... 530/350
(58) Field of Search ................................ 530/350, 300, 530/324, 325, 326, 327, 328, 329, 330; 424/184.1, 185.1

(56) References Cited

U.S. PATENT DOCUMENTS 5,919,912 A * 7/1999 Korneluk et al. ........ 530/389.2
6,020,127 A * 2/2000 MacKenzie et al. ............ 435/6

FOREIGN PATENT DOCUMENTS

| WO | WO 96/12016 | * | 4/1996 |
| WO | WO 97/26331 | * | 7/1997 |

OTHER PUBLICATIONS

Bowie et al., Science, 1990, 247:1306–1310.*
Burgess et al., J of Cell Bio. 111:2129–2138, 1990.*
Lazar et al., Moleular and Cellular Biology, 1988, 8:1247–1252.*
Bork, Genome Research, 2000, 10:398–400.*

* cited by examiner

*Primary Examiner*—Susan Ungar
(74) *Attorney, Agent, or Firm*—Wenderoth, Lind & Ponack, L.L.P.

(57) ABSTRACT

Novel apoptosis inhibitory proteins, a gene encoding the proteins and the cDNAs thereof are provided. More particularly, human apoptosis inhibitory proteins comprising the amino acid sequence of SQ ID No.1 or 3, a human gene encoding the human apoptosis inhibitory proteins and the cDNAs of the human gene comprising at least the nucleotide sequence for the coding region of SQ ID No.2 or 4, are provided.

4 Claims, 1 Drawing Sheet

SEQUENCE LISTING

<160> NUMBER OF SEQ ID NOS: 8

<210> SEQ ID NO 1
<211> LENGTH: 1403
<212> TYPE: PRT
<213> ORGANISM: Homo sapiens

<400> SEQUENCE: 1

```
Met Ala Thr Gln Gln Lys Ala Ser Asp Glu Arg Ile Ser Gln Phe Asp
 1               5                  10                  15

His Asn Leu Leu Pro Glu Leu Ser Ala Leu Leu Gly Leu Asp Ala Val
                20                  25                  30

Gln Leu Ala Lys Glu Leu Glu Glu Glu Gln Lys Glu Arg Ala Lys
            35                  40                  45

Met Gln Lys Gly Tyr Asn Ser Gln Met Arg Ser Glu Ala Lys Arg Leu
    50                  55                  60

Lys Thr Phe Val Thr Tyr Glu Pro Tyr Ser Ser Trp Ile Pro Gln Glu
65                  70                  75                  80

Met Ala Ala Ala Gly Phe Tyr Phe Thr Gly Val Lys Ser Gly Ile Gln
                85                  90                  95

Cys Phe Cys Cys Ser Leu Ile Leu Phe Gly Ala Gly Leu Thr Arg Leu
            100                 105                 110

Pro Ile Glu Asp His Lys Arg Phe His Pro Asp Cys Gly Phe Leu Leu
        115                 120                 125

Asn Lys Asp Val Gly Asn Ile Ala Lys Tyr Asp Ile Arg Val Lys Asn
    130                 135                 140

Leu Lys Ser Arg Leu Arg Gly Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
        195                 200                 205

Glu Gly Asp Asp Pro Trp Lys Glu His Ala Lys Trp Phe Pro Lys Cys
    210                 215                 220

Glu Phe Leu Arg Ser Lys Lys Ser Ser Glu Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
```

```
                  260                 265                 270
Ser Ile Phe Ala Tyr Glu Glu Leu Arg Leu Asp Ser Phe Lys Asp Trp
            275                 280                 285

Pro Arg Glu Ser Ala Val Gly Val Ala Ala Leu Ala Lys Ala Gly Leu
        290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
                325                 330                 335

Arg Cys Phe Pro Asn Cys Pro Phe Leu Gln Asn Met Lys Ser Ser Ala
            340                 345                 350

Glu Val Thr Pro Asp Leu Gln Ser Arg Gly Glu Leu Cys Glu Leu Leu
        355                 360                 365

Glu Thr Thr Ser Glu Ser Asn Leu Glu Asp Ser Ile Ala Val Gly Pro
    370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
                405                 410                 415

Arg His Met Ser Leu Leu Asp Ile Ser Ser Asp Leu Ala Thr Asp His
            420                 425                 430

Leu Leu Gly Cys Asp Leu Ser Ile Ala Ser Lys His Ile Ser Lys Pro
        435                 440                 445

Val Gln Glu Pro Leu Val Leu Pro Glu Val Phe Gly Asn Leu Asn Ser
    450                 455                 460

Val Met Cys Val Glu Gly Glu Ala Gly Ser Gly Lys Thr Val Leu Leu
465                 470                 475                 480

Lys Lys Ile Ala Phe Leu Trp Ala Ser Gly Cys Cys Pro Leu Leu Asn
                485                 490                 495

Arg Phe Gln Leu Val Phe Tyr Leu Ser Leu Ser Ser Thr Arg Pro Asp
            500                 505                 510

Glu Gly Leu Ala Ser Ile Ile Cys Asp Gln Leu Leu Glu Lys Glu Gly
        515                 520                 525

Ser Val Thr Glu Met Cys Met Arg Asn Ile Ile Gln Gln Leu Lys Asn
    530                 535                 540

Gln Val Leu Phe Leu Leu Asp Asp Tyr Lys Glu Ile Cys Ser Ile Pro
545                 550                 555                 560

Gln Val Ile Gly Lys Leu Ile Gln Lys Asn His Leu Ser Arg Thr Cys
                565                 570                 575

Leu Leu Ile Ala Val Arg Thr Asn Arg Ala Arg Asp Ile Arg Arg Tyr
            580                 585                 590

Leu Glu Thr Ile Leu Glu Ile Lys Ala Phe Pro Phe Tyr Asn Thr Val
        595                 600                 605

Cys Ile Leu Arg Lys Leu Phe Ser His Asn Met Thr Arg Leu Arg Lys
    610                 615                 620

Phe Met Val Tyr Phe Gly Lys Asn Gln Ser Leu Gln Lys Ile Gln Lys
625                 630                 635                 640

Thr Pro Leu Phe Val Ala Ala Ile Cys Ala His Trp Phe Gln Tyr Pro
                645                 650                 655

Phe Asp Pro Ser Phe Asp Asp Val Ala Val Phe Lys Ser Tyr Met Glu
            660                 665                 670

Arg Leu Ser Leu Arg Asn Lys Ala Thr Ala Glu Ile Leu Lys Ala Thr
        675                 680                 685
```

-continued

```
Val Ser Ser Cys Gly Glu Leu Ala Leu Lys Gly Phe Phe Ser Cys Cys
    690                 695                 700
Phe Glu Phe Asn Asp Asp Leu Ala Glu Ala Gly Val Asp Glu Asp
705                 710                 715                 720
Glu Asp Leu Thr Met Cys Leu Met Ser Lys Phe Thr Ala Gln Arg Leu
                725                 730                 735
Arg Pro Phe Tyr Arg Phe Leu Ser Pro Ala Phe Gln Glu Phe Leu Ala
                740                 745                 750
Gly Met Arg Leu Ile Glu Leu Leu Asp Ser Asp Arg Gln Glu His Gln
            755                 760                 765
Asp Leu Gly Leu Tyr His Leu Lys Gln Ile Asn Ser Pro Met Met Thr
    770                 775                 780
Val Ser Ala Tyr Asn Asn Phe Leu Asn Tyr Val Ser Ser Leu Pro Ser
785                 790                 795                 800
Thr Lys Ala Gly Pro Lys Ile Val Ser His Leu Leu His Leu Val Asp
                805                 810                 815
Asn Lys Glu Ser Leu Glu Asn Ile Ser Glu Asn Asp Asp Tyr Leu Lys
            820                 825                 830
His Gln Pro Glu Ile Ser Leu Gln Met Gln Leu Leu Arg Gly Leu Trp
    835                 840                 845
Gln Ile Cys Pro Gln Ala Tyr Phe Ser Met Val Ser Glu His Leu Leu
850                 855                 860
Val Leu Ala Leu Lys Thr Ala Tyr Gln Ser Asn Thr Val Ala Ala Cys
865                 870                 875                 880
Ser Pro Phe Val Leu Gln Phe Leu Gln Gly Arg Thr Leu Thr Leu Gly
                885                 890                 895
Ala Leu Asn Leu Gln Tyr Phe Phe Asp His Pro Glu Ser Leu Ser Leu
            900                 905                 910
Leu Arg Ser Ile His Phe Pro Ile Arg Gly Asn Lys Thr Ser Pro Arg
    915                 920                 925
Ala His Phe Ser Val Leu Glu Thr Cys Phe Asp Lys Ser Gln Val Pro
    930                 935                 940
Thr Ile Asp Gln Asp Tyr Ala Ser Ala Phe Glu Pro Met Asn Glu Trp
945                 950                 955                 960
Glu Arg Asn Leu Ala Glu Lys Glu Asp Asn Val Lys Ser Tyr Met Asp
                965                 970                 975
Met Gln Arg Arg Ala Ser Pro Asp Leu Ser Thr Gly Tyr Trp Lys Leu
            980                 985                 990
Ser Pro Lys Gln Tyr Lys Ile Pro Cys Leu Glu Val Asp Val Asn Asp
    995                 1000                1005
Ile Asp Val Val Gly Gln Asp Met Leu Glu Ile Leu Met Thr Val Phe
    1010                1015                1020
Ser Ala Ser Gln Arg Ile Glu Leu His Leu Asn His Ser Arg Gly Phe
1025                1030                1035                1040
Ile Glu Ser Ile Arg Pro Ala Leu Glu Leu Ser Lys Ala Ser Val Thr
                1045                1050                1055
Lys Cys Ser Ile Ser Lys Leu Glu Leu Ser Ala Ala Glu Gln Glu Leu
            1060                1065                1070
Leu Leu Thr Leu Pro Ser Leu Glu Ser Leu Glu Val Ser Gly Thr Ile
        1075                1080                1085
Gln Ser Gln Asp Gln Ile Phe Pro Asn Leu Asp Lys Phe Leu Cys Leu
    1090                1095                1100
```

-continued

```
Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
            1125                1130                1135

Gln Ile Ser Ala Glu Tyr Asp Pro Ser Lys Leu Val Lys Leu Ile Gln
        1140                1145                1150

Asn Ser Pro Asn Leu His Val Phe His Leu Lys Cys Asn Phe Phe Ser
    1155                1160                1165

Asp Phe Gly Ser Leu Met Thr Met Leu Val Ser Cys Lys Lys Leu Thr
   1170                1175                1180

Glu Ile Lys Phe Ser Asp Ser Phe Gln Ala Val Pro Phe Val Ala
1185                1190                1195                1200

Ser Leu Pro Asn Phe Ile Ser Leu Lys Ile Leu Asn Leu Glu Gly Gln
                1205                1210                1215

Gln Phe Pro Asp Glu Glu Thr Ser Glu Lys Phe Ala Tyr Ile Leu Gly
            1220                1225                1230

Ser Leu Ser Asn Leu Glu Glu Leu Ile Leu Pro Thr Gly Asp Gly Ile
        1235                1240                1245

Tyr Arg Val Ala Lys Leu Ile Ile Gln Gln Cys Gln Gln Leu His Cys
1250                1255                1260

Leu Arg Val Leu Ser Phe Phe Lys Thr Leu Asn Asp Asp Ser Val Val
1265                1270                1275                1280

Glu Ile Ala Lys Val Ala Ile Ser Gly Gly Phe Gln Lys Leu Glu Asn
            1285                1290                1295

Leu Lys Leu Ser Ile Asn His Lys Ile Thr Glu Glu Gly Tyr Arg Asn
        1300                1305                1310

Phe Phe Gln Ala Leu Asp Asn Met Pro Asn Leu Gln Glu Leu Asp Ile
    1315                1320                1325

Ser Arg His Phe Thr Glu Cys Ile Lys Ala Gln Ala Thr Thr Val Lys
   1330                1335                1340

Ser Leu Ser Gln Cys Val Leu Arg Leu Pro Arg Leu Ile Arg Leu Asn
1345                1350                1355                1360

Met Leu Ser Trp Leu Leu Asp Ala Asp Asp Ile Ala Leu Leu Asn Val
            1365                1370                1375

Met Lys Glu Arg His Pro Gln Ser Lys Tyr Leu Thr Ile Leu Gln Lys
        1380                1385                1390

Trp Ile Leu Pro Phe Ser Pro Ile Ile Gln Lys
        1395                1400

<210> SEQ ID NO 2
<211> LENGTH: 5984
<212> TYPE: DNA
<213> ORGANISM: Homo sapiens
<220> FEATURE:
<221> NAME/KEY: CDS
<222> LOCATION: (292)..(4500)

<400> SEQUENCE: 2
acaaaaggtc ctgtgctcac ctgggaccct tctggacgtt gccctgtgtt cctcttcgcc     60
tgcctgttca tctacgacga accccgggta ttgaccccag acaacaatgc cacttcatat    120
tggggacttc gtctgggatt ccaaggtgca ttcattgcaa agttccttaa atatttctc    180 actgcttcct actaaaggac ggacagagca tttgttcttc agccacatac tttccttcca    240
ctggccagca ttctcctcta ttagactaga actgtggata aacctcagaa a atg gcc    297
                                                         Met Ala
                                                           1
```

```
acc cag cag aaa gcc tct gac gag agg atc tcc cag ttt gat cac aat    345
Thr Gln Gln Lys Ala Ser Asp Glu Arg Ile Ser Gln Phe Asp His Asn
         5                  10                  15 ttg ctg cca gag ctg tct gct ctt ctg ggc cta gat gca gtt cag ttg    393
Leu Leu Pro Glu Leu Ser Ala Leu Leu Gly Leu Asp Ala Val Gln Leu
        20                  25                  30 gca aag gaa cta gaa gaa gag gag cag aag gag cga gca aaa atg cag    441
Ala Lys Glu Leu Glu Glu Glu Glu Gln Lys Glu Arg Ala Lys Met Gln
 35                  40                  45                  50 aaa ggc tac aac tct caa atg cgc agt gaa gca aaa agg tta aag act    489
Lys Gly Tyr Asn Ser Gln Met Arg Ser Glu Ala Lys Arg Leu Lys Thr
                     55                  60                  65 ttt gtg act tat gag ccg tac agc tca tgg ata cca cag gag atg gcg    537
Phe Val Thr Tyr Glu Pro Tyr Ser Ser Trp Ile Pro Gln Glu Met Ala
                 70                  75                  80 gcc gct ggg ttt tac ttc act ggg gta aaa tct ggg att cag tgc ttc    585
Ala Ala Gly Phe Tyr Phe Thr Gly Val Lys Ser Gly Ile Gln Cys Phe
             85                  90                  95 tgc tgt agc cta atc ctc ttt ggt gcc ggc ctc acg aga ctc ccc ata    633
Cys Cys Ser Leu Ile Leu Phe Gly Ala Gly Leu Thr Arg Leu Pro Ile
100                 105                 110 gaa gac cac aag agg ttt cat cca gat tgt ggg ttc ctt ttg aac aag    681
Glu Asp His Lys Arg Phe His Pro Asp Cys Gly Phe Leu Leu Asn Lys
115                 120                 125                 130 gat gtt ggt aac att gcc aag tac gac ata agg gtg aag aat ctg aag    729
Asp Val Gly Asn Ile Ala Lys Tyr Asp Ile Arg Val Lys Asn Leu Lys
                135                 140                 145 agc agg ctg aga gga ggt aaa atg agg tac caa gaa gag gag gct aga    777
Ser Arg Leu Arg Gly Gly Lys Met Arg Tyr Gln Glu Glu Glu Ala Arg
            150                 155                 160 ctt gca tcc ttc agg aac tgg cca ttt tat gtc caa ggg ata tcc cct    825
Leu Ala Ser Phe Arg Asn Trp Pro Phe Tyr Val Gln Gly Ile Ser Pro
        165                 170                 175 tgt gtg ctc tca gag gct ggc ttt gtc ttt aca ggt aaa cag gac acg    873
Cys Val Leu Ser Glu Ala Gly Phe Val Phe Thr Gly Lys Gln Asp Thr
    180                 185                 190 gta cag tgt ttt tcc tgt ggt gga tgt tta gga aat tgg gaa gaa gga    921
Val Gln Cys Phe Ser Cys Gly Gly Cys Leu Gly Asn Trp Glu Glu Gly
195                 200                 205                 210 gat gat cct tgg aag gaa cat gcc aaa tgg ttc ccc aaa tgt gaa ttt    969
Asp Asp Pro Trp Lys Glu His Ala Lys Trp Phe Pro Lys Cys Glu Phe
                215                 220                 225 ctt cgg agt aag aaa tcc tca gag gaa att acc cag tat att caa agc   1017
Leu Arg Ser Lys Lys Ser Ser Glu Glu Ile Thr Gln Tyr Ile Gln Ser
            230                 235                 240 tac aag gga ttt gtt gac ata acg gga gaa cat ttt gtg aat tcc tgg   1065
Tyr Lys Gly Phe Val Asp Ile Thr Gly Glu His Phe Val Asn Ser Trp
        245                 250                 255 gtc cag aga gaa tta cct atg gca tca gct tat tgc aat gac agc atc   1113
Val Gln Arg Glu Leu Pro Met Ala Ser Ala Tyr Cys Asn Asp Ser Ile
    260                 265                 270 ttt gct tac gaa gaa cta cgg ctg gac tct ttt aag gac tgg ccc cgg   1161
Phe Ala Tyr Glu Glu Leu Arg Leu Asp Ser Phe Lys Asp Trp Pro Arg
275                 280                 285                 290 gaa tca gct gtg gga gtt gca gca ctg gcc aaa gca ggt ctt ttc tac   1209
Glu Ser Ala Val Gly Val Ala Ala Leu Ala Lys Ala Gly Leu Phe Tyr
                295                 300                 305 aca ggt ata aag gac atc gtc cag tgc ttt tcc tgt gga ggg tgt tta   1257
Thr Gly Ile Lys Asp Ile Val Gln Cys Phe Ser Cys Gly Gly Cys Leu
```

```
                    310                 315                 320
gag aaa tgg cag gaa ggt gat gac cca tta gac gat cac acc aga tgt       1305
Glu Lys Trp Gln Glu Gly Asp Asp Pro Leu Asp Asp His Thr Arg Cys
        325                 330                 335 ttt ccc aat tgt cca ttt ctc caa aat atg aag tcc tct gcg gaa gtg       1353
Phe Pro Asn Cys Pro Phe Leu Gln Asn Met Lys Ser Ser Ala Glu Val
        340                 345                 350 act cca gac ctt cag agc cgt ggt gaa ctt tgt gaa tta ctg gaa acc       1401
Thr Pro Asp Leu Gln Ser Arg Gly Glu Leu Cys Glu Leu Leu Glu Thr
355                 360                 365                 370 aca agt gaa agc aat ctt gaa gat tca ata gca gtt ggt cct ata gtg       1449
Thr Ser Glu Ser Asn Leu Glu Asp Ser Ile Ala Val Gly Pro Ile Val
                375                 380                 385 cca gaa atg gca cag ggt gaa gcc cag tgg ttt caa gag gca aag aat       1497
Pro Glu Met Ala Gln Gly Glu Ala Gln Trp Phe Gln Glu Ala Lys Asn
                390                 395                 400 ctg aat gag cag ctg aga gca gct tat acc agc gcc agt ttc cgc cac       1545
Leu Asn Glu Gln Leu Arg Ala Ala Tyr Thr Ser Ala Ser Phe Arg His
        405                 410                 415 atg tct ttg ctt gat atc tct tcc gat ctg gcc acg gac cac ttg ctg       1593
Met Ser Leu Leu Asp Ile Ser Ser Asp Leu Ala Thr Asp His Leu Leu
        420                 425                 430 ggc tgt gat ctg tct att gct tca aaa cac atc agc aaa cct gtg caa       1641
Gly Cys Asp Leu Ser Ile Ala Ser Lys His Ile Ser Lys Pro Val Gln
435                 440                 445                 450 gaa cct ctg gtg ctg cct gag gtc ttt ggc aac ttg aac tct gtc atg       1689
Glu Pro Leu Val Leu Pro Glu Val Phe Gly Asn Leu Asn Ser Val Met
                455                 460                 465 tgt gtg gag ggt gaa gct gga agt gga aag acg gtc ctc ctg aag aaa       1737
Cys Val Glu Gly Glu Ala Gly Ser Gly Lys Thr Val Leu Leu Lys Lys
                470                 475                 480 ata gct ttt ctg tgg gca tct gga tgc tgt ccc ctg tta aac agg ttc       1785
Ile Ala Phe Leu Trp Ala Ser Gly Cys Cys Pro Leu Leu Asn Arg Phe
        485                 490                 495 cag ctg gtt ttc tac ctc tcc ctt agt tcc acc aga cca gac gag ggg       1833
Gln Leu Val Phe Tyr Leu Ser Leu Ser Ser Thr Arg Pro Asp Glu Gly
        500                 505                 510 ctg gcc agt atc atc tgt gac cag ctc cta gag aaa gaa gga tct gtt       1881
Leu Ala Ser Ile Ile Cys Asp Gln Leu Leu Glu Lys Glu Gly Ser Val
515                 520                 525                 530 act gaa atg tgc atg agg aac att atc cag cag tta aag aat cag gtc       1929
Thr Glu Met Cys Met Arg Asn Ile Ile Gln Gln Leu Lys Asn Gln Val
                535                 540                 545 tta ttc ctt tta gat gac tac aaa gaa ata tgt tca atc cct caa gtc       1977
Leu Phe Leu Leu Asp Asp Tyr Lys Glu Ile Cys Ser Ile Pro Gln Val
        550                 555                 560 ata gga aaa ctg att caa aaa aac cac tta tcc cgg acc tgc cta ttg       2025
Ile Gly Lys Leu Ile Gln Lys Asn His Leu Ser Arg Thr Cys Leu Leu
        565                 570                 575 att gct gtc cgt aca aac agg gcc agg gac atc cgc cga tac cta gag       2073
Ile Ala Val Arg Thr Asn Arg Ala Arg Asp Ile Arg Arg Tyr Leu Glu
        580                 585                 590 acc att cta gag atc aaa gca ttt ccc ttt tat aat act gtc tgt ata       2121
Thr Ile Leu Glu Ile Lys Ala Phe Pro Phe Tyr Asn Thr Val Cys Ile
595                 600                 605                 610 tta cgg aag ctc ttt tca cat aat atg act cgt ctg cga aag ttt atg       2169
Leu Arg Lys Leu Phe Ser His Asn Met Thr Arg Leu Arg Lys Phe Met
                615                 620                 625 gtt tac ttt gga aag aac caa agt ttg cag aag ata cag aaa act cct       2217
```

```
Val Tyr Phe Gly Lys Asn Gln Ser Leu Gln Lys Ile Gln Lys Thr Pro
            630                 635                 640 ctc ttt gtg gcg gcg atc tgt gct cat tgg ttt cag tat cct ttt gac    2265
Leu Phe Val Ala Ala Ile Cys Ala His Trp Phe Gln Tyr Pro Phe Asp
            645                 650                 655 cca tcc ttt gat gat gtg gct gtt ttc aag tcc tat atg gaa cgc ctt    2313
Pro Ser Phe Asp Asp Val Ala Val Phe Lys Ser Tyr Met Glu Arg Leu
            660                 665                 670 tcc tta agg aac aaa gcg aca gct gaa att ctc aaa gca act gtg tcc    2361
Ser Leu Arg Asn Lys Ala Thr Ala Glu Ile Leu Lys Ala Thr Val Ser
675                 680                 685                 690 tcc tgt ggt gag ctg gcc ttg aaa ggg ttt ttt tca tgt tgc ttt gag    2409
Ser Cys Gly Glu Leu Ala Leu Lys Gly Phe Phe Ser Cys Cys Phe Glu
                695                 700                 705 ttt aat gat gat gat ctc gca gaa gca ggg gtt gat gaa gat gaa gat    2457
Phe Asn Asp Asp Asp Leu Ala Glu Ala Gly Val Asp Glu Asp Glu Asp
            710                 715                 720 cta acc atg tgc ttg atg agc aaa ttt aca gcc cag aga cta aga cca    2505
Leu Thr Met Cys Leu Met Ser Lys Phe Thr Ala Gln Arg Leu Arg Pro
            725                 730                 735 ttc tac cgg ttt tta agt cct gcc ttc caa gaa ttt ctt gcg ggg atg    2553
Phe Tyr Arg Phe Leu Ser Pro Ala Phe Gln Glu Phe Leu Ala Gly Met
            740                 745                 750 agg ctg att gaa ctc ctg gat tca gat agg cag gaa cat caa gat ttg    2601
Arg Leu Ile Glu Leu Leu Asp Ser Asp Arg Gln Glu His Gln Asp Leu
755                 760                 765                 770 gga ctg tat cat ttg aaa caa atc aac tca ccc atg atg act gta agc    2649
Gly Leu Tyr His Leu Lys Gln Ile Asn Ser Pro Met Met Thr Val Ser
                775                 780                 785 gcc tac aac aat ttt ttg aac tat gtc tcc agc ctc cct tca aca aaa    2697
Ala Tyr Asn Asn Phe Leu Asn Tyr Val Ser Ser Leu Pro Ser Thr Lys
            790                 795                 800 gca ggg ccc aaa att gtg tct cat ttg ctc cat tta gtg gat aac aaa    2745
Ala Gly Pro Lys Ile Val Ser His Leu Leu His Leu Val Asp Asn Lys
            805                 810                 815 gag tca ttg gag aat ata tct gaa aat gat gac tac tta aag cac cag    2793
Glu Ser Leu Glu Asn Ile Ser Glu Asn Asp Asp Tyr Leu Lys His Gln
            820                 825                 830 cca gaa att tca ctg cag atg cag tta ctt agg gga ttg tgg caa att    2841
Pro Glu Ile Ser Leu Gln Met Gln Leu Leu Arg Gly Leu Trp Gln Ile
835                 840                 845                 850 tgt cca caa gct tac ttt tca atg gtt tca gaa cat tta ctg gtt ctt    2889
Cys Pro Gln Ala Tyr Phe Ser Met Val Ser Glu His Leu Leu Val Leu
                855                 860                 865 gcc ctg aaa act gct tat caa agc aac act gtt gct gcg tgt tct cca    2937
Ala Leu Lys Thr Ala Tyr Gln Ser Asn Thr Val Ala Ala Cys Ser Pro
            870                 875                 880 ttt gtt ttg caa ttc ctt caa ggg aga aca ctg act ttg ggt gcg ctt    2985
Phe Val Leu Gln Phe Leu Gln Gly Arg Thr Leu Thr Leu Gly Ala Leu
            885                 890                 895 aac tta cag tac ttt ttc gac cac cca gaa agc ttg tca ttg ttg agg    3033
Asn Leu Gln Tyr Phe Phe Asp His Pro Glu Ser Leu Ser Leu Leu Arg
            900                 905                 910 agc atc cac ttc cca ata cga gga aat aag aca tca ccc aga gca cat    3081
Ser Ile His Phe Pro Ile Arg Gly Asn Lys Thr Ser Pro Arg Ala His
915                 920                 925                 930 ttt tca gtt ctg gaa aca tgt ttt gac aaa tca cag gtg cca act ata    3129
Phe Ser Val Leu Glu Thr Cys Phe Asp Lys Ser Gln Val Pro Thr Ile
            935                 940                 945
```

-continued

| | |
|---|---|
| gat cag gac tat gct tct gcc ttt gaa cct atg aat gaa tgg gag cga<br>Asp Gln Asp Tyr Ala Ser Ala Phe Glu Pro Met Asn Glu Trp Glu Arg<br>950                                 955                          960 | 3177 |
| aat tta gct gaa aaa gag gat aat gta aag agc tat atg gat atg cag<br>Asn Leu Ala Glu Lys Glu Asp Asn Val Lys Ser Tyr Met Asp Met Gln<br>       965                           970                            975 | 3225 |
| cgc agg gca tca cca gac ctt agt act ggc tat tgg aaa ctt tct cca<br>Arg Arg Ala Ser Pro Asp Leu Ser Thr Gly Tyr Trp Lys Leu Ser Pro<br>980                                 985                          990 | 3273 |
| aag cag tac aag att ccc tgt cta gaa gtc gat gtg aat gat att gat<br>Lys Gln Tyr Lys Ile Pro Cys Leu Glu Val Asp Val Asn Asp Ile Asp<br>995                       1000                       1005                 1010 | 3321 |
| gtt gta ggc cag gat atg ctt gag att cta atg aca gtt ttc tca gct<br>Val Val Gly Gln Asp Met Leu Glu Ile Leu Met Thr Val Phe Ser Ala<br>                1015                       1020                      1025 | 3369 |
| tca cag cgc atc gaa ctc cat tta aac cac agc aga ggc ttt ata gaa<br>Ser Gln Arg Ile Glu Leu His Leu Asn His Ser Arg Gly Phe Ile Glu<br>       1030                       1035                       1040 | 3417 |
| agc atc cgc cca gct ctt gag ctg tct aag gcc tct gtc acc aag tgc<br>Ser Ile Arg Pro Ala Leu Glu Leu Ser Lys Ala Ser Val Thr Lys Cys<br>1045                       1050                      1055 | 3465 |
| tcc ata agc aag ttg gaa ctc agc gca gcc gaa cag gaa ctg ctt ctc<br>Ser Ile Ser Lys Leu Glu Leu Ser Ala Ala Glu Gln Glu Leu Leu Leu<br>     1060                     1065                     1070 | 3513 |
| acc ctg cct tcc ctg gaa tct ctt gaa gtc tca ggg aca atc cag tca<br>Thr Leu Pro Ser Leu Glu Ser Leu Glu Val Ser Gly Thr Ile Gln Ser<br>1075                   1080                     1085                  1090 | 3561 |
| caa gac caa atc ttt cct aat ctg gat aag ttc ctg tgc ctg aaa gaa<br>Gln Asp Gln Ile Phe Pro Asn Leu Asp Lys Phe Leu Cys Leu Lys Glu<br>             1095                     1100                   1105 | 3609 |
| ctg tct gtg gat ctg gag ggc aat ata aat gtt ttt tca gtc att cct<br>Leu Ser Val Asp Leu Glu Gly Asn Ile Asn Val Phe Ser Val Ile Pro<br>        1110                     1115                      1120 | 3657 |
| gaa gaa ttt cca aac ttc cac cat atg gag aaa tta ttg atc caa att<br>Glu Glu Phe Pro Asn Phe His His Met Glu Lys Leu Leu Ile Gln Ile<br>1125                       1130                      1135 | 3705 |
| tca gct gag tat gat cct tcc aaa cta gta aaa tta att caa aat tct<br>Ser Ala Glu Tyr Asp Pro Ser Lys Leu Val Lys Leu Ile Gln Asn Ser<br>     1140                     1145                     1150 | 3753 |
| cca aac ctt cat gtt ttc cat ctg aag tgt aac ttc ttt tcg gat ttt<br>Pro Asn Leu His Val Phe His Leu Lys Cys Asn Phe Phe Ser Asp Phe<br>1155                       1160                      1165                 1170 | 3801 |
| ggg tct ctc atg act atg ctt gtt tcc tgt aag aaa ctc aca gaa att<br>Gly Ser Leu Met Thr Met Leu Val Ser Cys Lys Lys Leu Thr Glu Ile<br>                1175                       1180                      1185 | 3849 |
| aag ttt tcg gat tca ttt ttt caa gcc gtc cca ttt gtt gcc agt ttg<br>Lys Phe Ser Asp Ser Phe Phe Gln Ala Val Pro Phe Val Ala Ser Leu<br>             1190                     1195                     1200 | 3897 |
| cca aat ttt att tct ctg aag ata tta aat ctt gaa ggc cag caa ttt<br>Pro Asn Phe Ile Ser Leu Lys Ile Leu Asn Leu Glu Gly Gln Gln Phe<br>        1205                     1210                      1215 | 3945 |
| cct gat gag gaa aca tca gaa aaa ttt gcc tac att tta ggt tct ctt<br>Pro Asp Glu Glu Thr Ser Glu Lys Phe Ala Tyr Ile Leu Gly Ser Leu<br>1220                       1225                      1230 | 3993 |
| agt aac ctg gaa gaa ttg atc ctt cct act ggg gat gga att tat cga<br>Ser Asn Leu Glu Glu Leu Ile Leu Pro Thr Gly Asp Gly Ile Tyr Arg<br>1235                       1240                      1245                 1250 | 4041 |
| gtg gcc aaa ctg atc atc cag cag tgt cag cag ctt cat tgt ctc cga<br>Val Ala Lys Leu Ile Ile Gln Gln Cys Gln Gln Leu His Cys Leu Arg<br>                1255                       1260                      1265 | 4089 |

```
gtc ctc tca ttt ttc aag act ttg aat gat gac agc gtg gtg gaa att       4137
Val Leu Ser Phe Phe Lys Thr Leu Asn Asp Asp Ser Val Val Glu Ile
        1270                1275                1280 gcc aaa gta gca atc agt gga ggt ttc cag aaa ctt gag aac cta aag       4185
Ala Lys Val Ala Ile Ser Gly Gly Phe Gln Lys Leu Glu Asn Leu Lys
        1285                1290                1295 ctt tca atc aat cac aag att aca gag gaa gga tac aga aat ttc ttt       4233
Leu Ser Ile Asn His Lys Ile Thr Glu Glu Gly Tyr Arg Asn Phe Phe
        1300                1305                1310 caa gca ctg gac aac atg cca aac ttg cag gag ttg gac atc tcc agg       4281
Gln Ala Leu Asp Asn Met Pro Asn Leu Gln Glu Leu Asp Ile Ser Arg
1315                1320                1325                1330 cat ttc aca gag tgt atc aaa gct cag gcc aca aca gtc aag tct ttg       4329
His Phe Thr Glu Cys Ile Lys Ala Gln Ala Thr Thr Val Lys Ser Leu
        1335                1340                1345 agt caa tgt gtg tta cga cta cca agg ctc att aga ctg aac atg tta       4377
Ser Gln Cys Val Leu Arg Leu Pro Arg Leu Ile Arg Leu Asn Met Leu
        1350                1355                1360 agt tgg ctc ttg gat gca gat gat att gca ttg ctt aat gtc atg aaa       4425
Ser Trp Leu Leu Asp Ala Asp Asp Ile Ala Leu Leu Asn Val Met Lys
        1365                1370                1375 gaa aga cat cct caa tct aag tac tta act att ctc cag aaa tgg ata       4473
Glu Arg His Pro Gln Ser Lys Tyr Leu Thr Ile Leu Gln Lys Trp Ile
        1380                1385                1390 ctg ccg ttc tct cca atc att cag aaa taa aagattcagc taaaaactgc        4523
Leu Pro Phe Ser Pro Ile Ile Gln Lys
1395                1400 tgaatcaata atttgtcttg gggcatattg aggatgtaaa aaaagttgtt gattaatgct    4583
aaaaaccaaa ttatccaaaa ttattttatt aaatattgca tacaaaagaa aatgtgtaag    4643
gcttgctaaa aaacaaaaca aaacaaaaca cagtcctgca tactcaccac caagctcaag    4703
aaataaatca tcaccaatac ctttgaggtc cctgagtaat ccaccccagc taaaggcaaa    4763
cccttcaatc aagtttatac agcaaaccct ccattgtcca tggtcaacag ggaaggggtt    4823
ggggacaggt ctgccaatct atctaaaagc cacaatatgg aagaagtatt caatttatat    4883
aataaatggc taacttaacg gttgaatcac tttcatacat ggatgaaacg ggtttaacac    4943
aggatccaca tgaatcttct gtgggccaaa atatgttcct taatccttgt agaacctgtc    5003
ttctatattg aactagcttt ggtacagtag agttaactta ctttccattt atccactgcc    5063
aatataaaga ggaaacaggg gttagggaaa atgacttca ttccagaggc ttctcagagt     5123
tcaacatatg ctataattta gaattttctt atgaatccac tctacttggg tagaaaatat    5183
tttatctcta gtgattgcat attatttcca tatcatagta tttcatagta ttatatttga    5243
tatgagtgtc tatatcaatg tcagtgtcca gaatttcgtt cctaccagtt gagtagtttt    5303
ctgaacggcc agaagaccat tcgaaattca tgatactact ataagttggt aaacaaccat    5363
acttttatcc tcattttat tctcactaag aaaaaagtca actcccctcc ccttgcccaa     5423
gtatgaaata tagggacagt atgtatggtg tggtctcatt tgtttagaaa accacttatg    5483
actgggtgcg gtggctcaca cctgtaatcc cagcactttg ggaggctgag gcgggcgaat    5543
catttgaggt gaggagttcg agaccggcct ggccagcatg gtgaaacccc attttgcta    5603 aagtacaaaa aattagccag gtgtggtggc acatgcctgt ggtcccagcc actggggcgg    5663
ctgagacgca ggacttgctt gaacccggga ggcagaggtt gcagtgagcc gagatggcgc    5723
cactgcattc cagcctgggc aacagagcaa gaccctgtct gtttcaaaac aaaaaacaaa    5783
```

```
accacttata ttgctagcta cattaagaat ttctgaatat gttactgagc ttgcttgtgg    5843
taaccattta taatatcaga aagtatatgt acaccaaaac atgttgaaca tccatgttgt    5903
acaactgaaa tataaataat tttgtcaatt atacctaaat aaaactggaa aaaaaaaaa     5963 aaaaaaaaaa aaaaaaaaa a                                               5984
```

<210> SEQ ID NO 3
<211> LENGTH: 1295
<212> TYPE: PRT
<213> ORGANISM: Homo sapiens

<400> SEQUENCE: 3

```
Met Ala Thr Gln Gln Lys Ala Ser Asp Glu Arg Ile Ser Gln Phe Asp
 1               5                  10                  15

His Asn Leu Leu Pro Glu Leu Ser Ala Leu Leu Gly Leu Asp Ala Val
                20                  25                  30

Gln Leu Ala Lys Glu Leu Glu Glu Glu Gln Lys Glu Arg Ala Lys
         35                  40                  45

Met Gln Lys Gly Tyr Asn Ser Gln Met Arg Ser Glu Ala Lys Arg Leu
     50                  55                  60

Lys Thr Phe Val Thr Tyr Glu Pro Tyr Ser Ser Trp Ile Pro Gln Glu
 65                  70                  75                  80

Met Ala Ala Gly Phe Tyr Phe Thr Gly Val Lys Ser Gly Ile Gln
                 85                  90                  95

Cys Phe Cys Cys Ser Leu Ile Leu Phe Gly Ala Gly Leu Thr Arg Leu
                100                 105                 110

Pro Ile Glu Asp His Lys Arg Phe His Pro Asp Cys Gly Phe Leu Leu
            115                 120                 125

Asn Lys Asp Val Gly Asn Ile Ala Lys Tyr Asp Ile Arg Val Lys Asn
130                 135                 140

Leu Lys Ser Arg Leu Arg Gly Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
        195                 200                 205

Glu Gly Asp Asp Pro Trp Lys Glu His Ala Lys Trp Phe Pro Lys Cys
    210                 215                 220

Glu Phe Leu Arg Ser Lys Lys Ser Ser Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
            260                 265                 270

Ser Ile Phe Ala Tyr Glu Glu Leu Arg Leu Asp Ser Phe Lys Asp Trp
        275                 280                 285

Pro Arg Glu Ser Ala Val Gly Val Ala Ala Leu Ala Lys Ala Gly Leu
    290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
                325                 330                 335
```

```
Arg Cys Phe Pro Asn Cys Pro Phe Leu Gln Asn Met Lys Ser Ser Ala
        340                 345                 350

Glu Val Thr Pro Asp Leu Gln Ser Arg Gly Glu Leu Cys Glu Leu Leu
        355                 360                 365

Glu Thr Thr Ser Glu Ser Asn Leu Glu Asp Ser Ile Ala Val Gly Pro
        370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
            405                 410                 415

Arg His Met Ser Leu Leu Asp Ile Ser Ser Asp Leu Ala Thr Asp His
            420                 425                 430

Leu Leu Gly Cys Asp Leu Ser Ile Ala Ser Lys His Ile Ser Lys Pro
            435                 440                 445

Val Gln Glu Pro Leu Val Leu Pro Glu Val Phe Gly Asn Leu Asn Ser
            450                 455                 460

Val Met Cys Val Glu Gly Glu Ala Gly Ser Gly Lys Thr Val Leu Leu
465                 470                 475                 480

Lys Lys Ile Ala Phe Leu Trp Ala Ser Gly Cys Cys Pro Leu Leu Asn
                485                 490                 495

Arg Phe Gln Leu Val Phe Tyr Leu Ser Leu Ser Ser Thr Arg Pro Asp
            500                 505                 510

Glu Gly Leu Ala Ser Ile Ile Cys Asp Gln Leu Leu Glu Lys Glu Gly
            515                 520                 525

Ser Val Thr Glu Met Cys Met Arg Asn Ile Ile Gln Gln Leu Lys Asn
            530                 535                 540

Gln Val Leu Phe Leu Leu Asp Asp Tyr Lys Glu Ile Cys Ser Ile Pro
545                 550                 555                 560

Gln Val Ile Gly Lys Leu Ile Gln Lys Asn His Leu Ser Arg Thr Cys
                565                 570                 575

Leu Leu Ile Ala Val Arg Thr Asn Arg Ala Arg Asp Ile Arg Arg Tyr
            580                 585                 590

Leu Glu Thr Ile Leu Glu Ile Lys Ala Phe Pro Phe Tyr Asn Thr Val
            595                 600                 605

Cys Ile Leu Arg Lys Leu Phe Ser His Asn Met Thr Arg Leu Arg Lys
610                 615                 620

Phe Met Val Tyr Phe Gly Lys Asn Gln Ser Leu Gln Lys Ile Gln Lys
625                 630                 635                 640

Thr Pro Leu Phe Val Ala Ala Ile Cys Ala His Trp Phe Gln Tyr Pro
                645                 650                 655

Phe Asp Pro Ser Phe Asp Asp Val Ala Val Phe Lys Ser Tyr Met Glu
            660                 665                 670

Arg Leu Ser Leu Arg Asn Lys Ala Thr Ala Glu Ile Leu Lys Ala Thr
            675                 680                 685

Val Ser Ser Cys Gly Glu Leu Ala Leu Lys Gly Phe Phe Ser Cys Cys
            690                 695                 700

Phe Glu Phe Asn Asp Asp Asp Leu Ala Glu Ala Gly Val Asp Glu Asp
705                 710                 715                 720

Glu Asp Leu Thr Met Cys Leu Met Ser Lys Phe Thr Ala Gln Arg Leu
                725                 730                 735

Arg Pro Phe Tyr Arg Phe Leu Ser Pro Ala Phe Gln Glu Phe Leu Ala
            740                 745                 750

Gly Met Arg Leu Ile Glu Leu Leu Asp Ser Asp Arg Gln Glu His Gln
```

```
              755                 760                 765
Asp Leu Gly Leu Tyr His Leu Lys Gln Ile Asn Ser Pro Met Met Thr
        770                 775                 780

Val Ser Ala Tyr Asn Asn Phe Leu Asn Tyr Val Ser Ser Leu Pro Ser
785                 790                 795                 800

Thr Lys Ala Gly Pro Lys Ile Val Ser His Leu Leu His Leu Val Asp
                805                 810                 815

Asn Lys Glu Ser Leu Glu Asn Ile Ser Glu Asn Asp Asp Tyr Leu Lys
            820                 825                 830

His Gln Pro Glu Ile Ser Leu Gln Met Gln Leu Leu Arg Gly Leu Trp
        835                 840                 845

Gln Ile Cys Pro Gln Ala Tyr Phe Ser Met Val Ser Glu His Leu Leu
    850                 855                 860

Val Leu Ala Leu Lys Thr Ala Tyr Gln Ser Asn Thr Val Ala Ala Cys
865                 870                 875                 880

Ser Pro Phe Val Leu Gln Phe Leu Gln Gly Arg Thr Leu Thr Leu Gly
                885                 890                 895

Ala Leu Asn Leu Gln Tyr Phe Phe Asp His Pro Glu Ser Leu Ser Leu
            900                 905                 910

Leu Arg Ser Ile His Phe Pro Ile Arg Gly Asn Lys Thr Ser Pro Arg
        915                 920                 925

Ala His Phe Ser Val Leu Glu Thr Cys Phe Asp Lys Ser Gln Val Pro
    930                 935                 940

Thr Ile Asp Gln Asp Tyr Ala Ser Ala Phe Glu Pro Met Asn Glu Trp
945                 950                 955                 960

Glu Arg Asn Leu Ala Glu Lys Glu Asp Asn Val Lys Ser Tyr Met Asp
                965                 970                 975

Met Gln Arg Arg Ala Ser Pro Asp Leu Ser Thr Gly Tyr Trp Lys Leu
            980                 985                 990

Ser Pro Lys Gln Tyr Lys Ile Pro Cys Leu Glu Val Asp Val Asn Asp
        995                 1000                1005

Ile Asp Val Val Gly Gln Asp Met Leu Glu Ile Leu Met Thr Val Phe
    1010                1015                1020

Ser Ala Ser Gln Arg Ile Glu Leu His Leu Asn His Ser Arg Gly Phe
1025                1030                1035                1040

Ile Glu Ser Ile Arg Pro Ala Leu Glu Leu Ser Lys Ala Ser Val Thr
                1045                1050                1055

Lys Cys Ser Ile Ser Lys Leu Glu Leu Ser Ala Ala Glu Gln Glu Leu
            1060                1065                1070

Leu Leu Thr Leu Pro Ser Leu Glu Ser Leu Glu Val Ser Gly Thr Ile
        1075                1080                1085

Gln Ser Gln Asp Gln Ile Phe Pro Asn Leu Asp Lys Phe Leu Cys Leu
    1090                1095                1100

Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
                1125                1130                1135

Gln Ile Ser Ala Glu Tyr Asp Pro Ser Lys Leu Val Lys Leu Ile Gln
            1140                1145                1150

Asn Ser Pro Asn Leu His Val Phe His Leu Lys Cys Asn Phe Phe Ser
        1155                1160                1165

Asp Phe Gly Ser Leu Met Thr Met Leu Val Ser Cys Lys Lys Leu Thr
    1170                1175                1180
```

```
Glu Ile Lys Phe Ser Asp Ser Phe Phe Gln Ala Val Pro Phe Val Ala
1185                1190                1195                1200

Ser Leu Pro Asn Phe Ile Ser Leu Lys Ile Leu Asn Leu Glu Gly Gln
            1205                1210                1215

Gln Phe Pro Asp Glu Glu Thr Ser Glu Lys Phe Ala Tyr Ile Leu Gly
        1220                1225                1230

Ser Leu Ser Asn Leu Glu Glu Leu Ile Leu Pro Thr Gly Asp Gly Ile
        1235                1240                1245

Tyr Arg Val Ala Lys Leu Ile Ile Gln Gln Cys Gln Gln Leu His Cys
        1250                1255                1260

Leu Arg Val Leu Ser Phe Phe Lys Thr Leu Asn Asp Asp Ser Val Val
1265                1270                1275                1280

Glu Ile Gly Glu Leu Val Phe Gln Leu Ala Trp Lys Pro Val Val
                1285                1290                1295

<210> SEQ ID NO 4
<211> LENGTH: 5366
<212> TYPE: DNA
<213> ORGANISM: Homo sapiens
<220> FEATURE:
<221> NAME/KEY: CDS
<222> LOCATION: (292)..(4176)

<400> SEQUENCE: 4
acaaaaggtc ctgtgctcac ctgggaccct tctggacgtt gccctgtgtt cctcttcgcc      60
tgcctgttca tctacgacga accccgggta ttgaccccag acaacaatgc cacttcatat     120
tggggacttc gtctgggatt ccaaggtgca ttcattgcaa agttccttaa atattttctc     180
actgcttcct actaaaggac ggacagagca tttgttcttc agccacatac tttccttcca     240
ctggccagca ttctcctcta ttagactaga actgtggata aacctcagaa a atg gcc     297
                                                        Met Ala
                                                          1 acc cag cag aaa gcc tct gac gag agg atc tcc cag ttt gat cac aat       345
Thr Gln Gln Lys Ala Ser Asp Glu Arg Ile Ser Gln Phe Asp His Asn
         5                  10                  15 ttg ctg cca gag ctg tct gct ctt ctg ggc cta gat gca gtt cag ttg       393
Leu Leu Pro Glu Leu Ser Ala Leu Leu Gly Leu Asp Ala Val Gln Leu
     20                  25                  30 gca aag gaa cta gaa gaa gag gag cag aag gag cga gca aaa atg cag       441
Ala Lys Glu Leu Glu Glu Glu Glu Gln Lys Glu Arg Ala Lys Met Gln
 35                  40                  45                  50 aaa ggc tac aac tct caa atg cgc agt gaa gca aaa agg tta aag act       489
Lys Gly Tyr Asn Ser Gln Met Arg Ser Glu Ala Lys Arg Leu Lys Thr
                 55                  60                  65 ttt gtg act tat gag ccg tac agc tca tgg ata cca cag gag atg gcg       537
Phe Val Thr Tyr Glu Pro Tyr Ser Ser Trp Ile Pro Gln Glu Met Ala
             70                  75                  80 gcc gct ggg ttt tac ttc act ggg gta aaa tct ggg att cag tgc ttc       585
Ala Ala Gly Phe Tyr Phe Thr Gly Val Lys Ser Gly Ile Gln Cys Phe
         85                  90                  95 tgc tgt agc cta atc ctc ttt ggt gcc ggc ctc acg aga ctc ccc ata       633
Cys Cys Ser Leu Ile Leu Phe Gly Ala Gly Leu Thr Arg Leu Pro Ile
    100                 105                 110 gaa gac cac aag agg ttt cat cca gat tgt ggg ttc ctt ttg aac aag       681
Glu Asp His Lys Arg Phe His Pro Asp Cys Gly Phe Leu Leu Asn Lys
115                 120                 125                 130 gat gtt ggt aac att gcc aag tac gac ata agg gtg aag aat ctg aag       729
Asp Val Gly Asn Ile Ala Lys Tyr Asp Ile Arg Val Lys Asn Leu Lys
```

-continued

```
                 135                 140                 145
agc agg ctg aga gga ggt aaa atg agg tac caa gaa gag gag gct aga    777
Ser Arg Leu Arg Gly Gly Lys Met Arg Tyr Gln Glu Glu Glu Ala Arg
            150                 155                 160 ctt gca tcc ttc agg aac tgg cca ttt tat gtc caa ggg ata tcc cct    825
Leu Ala Ser Phe Arg Asn Trp Pro Phe Tyr Val Gln Gly Ile Ser Pro
        165                 170                 175 tgt gtg ctc tca gag gct ggc ttt gtc ttt aca ggt aaa cag gac acg    873
Cys Val Leu Ser Glu Ala Gly Phe Val Phe Thr Gly Lys Gln Asp Thr
    180                 185                 190 gta cag tgt ttt tcc tgt ggt gga tgt tta gga aat tgg gaa gaa gga    921
Val Gln Cys Phe Ser Cys Gly Gly Cys Leu Gly Asn Trp Glu Glu Gly
195                 200                 205                 210 gat gat cct tgg aag gaa cat gcc aaa tgg ttc ccc aaa tgt gaa ttt    969
Asp Asp Pro Trp Lys Glu His Ala Lys Trp Phe Pro Lys Cys Glu Phe
                215                 220                 225 ctt cgg agt aag aaa tcc tca gag gaa att acc cag tat att caa agc   1017
Leu Arg Ser Lys Lys Ser Ser Glu Glu Ile Thr Gln Tyr Ile Gln Ser
            230                 235                 240 tac aag gga ttt gtt gac ata acg gga gaa cat ttt gtg aat tcc tgg   1065
Tyr Lys Gly Phe Val Asp Ile Thr Gly Glu His Phe Val Asn Ser Trp
        245                 250                 255 gtc cag aga gaa tta cct atg gca tca gct tat tgc aat gac agc atc   1113
Val Gln Arg Glu Leu Pro Met Ala Ser Ala Tyr Cys Asn Asp Ser Ile
    260                 265                 270 ttt gct tac gaa gaa cta cgg ctg gac tct ttt aag gac tgg ccc cgg   1161
Phe Ala Tyr Glu Glu Leu Arg Leu Asp Ser Phe Lys Asp Trp Pro Arg
275                 280                 285                 290 gaa tca gct gtg gga gtt gca gca ctg gcc aaa gca ggt ctt ttc tac   1209
Glu Ser Ala Val Gly Val Ala Ala Leu Ala Lys Ala Gly Leu Phe Tyr
                295                 300                 305 aca ggt ata aag gac atc gtc cag tgc ttt tcc tgt gga ggg tgt tta   1257
Thr Gly Ile Lys Asp Ile Val Gln Cys Phe Ser Cys Gly Gly Cys Leu
            310                 315                 320 gag aaa tgg cag gaa ggt gat gac cca tta gac gat cac acc aga tgt   1305
Glu Lys Trp Gln Glu Gly Asp Asp Pro Leu Asp Asp His Thr Arg Cys
        325                 330                 335 ttt ccc aat tgt cca ttt ctc caa aat atg aag tcc tct gcg gaa gtg   1353
Phe Pro Asn Cys Pro Phe Leu Gln Asn Met Lys Ser Ser Ala Glu Val
    340                 345                 350 act cca gac ctt cag agc cgt ggt gaa ctt tgt gaa tta ctg gaa acc   1401
Thr Pro Asp Leu Gln Ser Arg Gly Glu Leu Cys Glu Leu Leu Glu Thr
355                 360                 365                 370 aca agt gaa agc aat ctt gaa gat tca ata gca gtt ggt cct ata gtg   1449
Thr Ser Glu Ser Asn Leu Glu Asp Ser Ile Ala Val Gly Pro Ile Val
                375                 380                 385 cca gaa atg gca cag ggt gaa gcc cag tgg ttt caa gag gca aag aat   1497
Pro Glu Met Ala Gln Gly Glu Ala Gln Trp Phe Gln Glu Ala Lys Asn
            390                 395                 400 ctg aat gag cag ctg aga gca gct tat acc agc gcc agt ttc gcc cac   1545
Leu Asn Glu Gln Leu Arg Ala Ala Tyr Thr Ser Ala Ser Phe Arg His
        405                 410                 415 atg tct ttg ctt gat atc tct tcc gat ctg gcc acg gac cac ttg ctg   1593
Met Ser Leu Leu Asp Ile Ser Ser Asp Leu Ala Thr Asp His Leu Leu
    420                 425                 430 ggc tgt gat ctg tct att gct tca aaa cac atc agc aaa cct gtg caa   1641
Gly Cys Asp Leu Ser Ile Ala Ser Lys His Ile Ser Lys Pro Val Gln
435                 440                 445                 450 gaa cct ctg gtg ctg cct gag gtc ttt ggc aac ttg aac tct gtc atg   1689
```

-continued

```
                    Glu Pro Leu Val Leu Pro Glu Val Phe Gly Asn Leu Asn Ser Val Met
                                    455                 460                 465 tgt gtg gag ggt gaa gct gga agt gga aag acg gtc ctc ctg aag aaa              1737
Cys Val Glu Gly Glu Ala Gly Ser Gly Lys Thr Val Leu Leu Lys Lys
                470                 475                 480 ata gct ttt ctg tgg gca tct gga tgc tgt ccc ctg tta aac agg ttc              1785
Ile Ala Phe Leu Trp Ala Ser Gly Cys Cys Pro Leu Leu Asn Arg Phe
                485                 490                 495 cag ctg gtt ttc tac ctc tcc ctt agt tcc acc aga cca gac gag ggg              1833
Gln Leu Val Phe Tyr Leu Ser Leu Ser Ser Thr Arg Pro Asp Glu Gly
            500                 505                 510 ctg gcc agt atc atc tgt gac cag ctc cta gag aaa gaa gga tct gtt              1881
Leu Ala Ser Ile Ile Cys Asp Gln Leu Leu Glu Lys Glu Gly Ser Val
515                 520                 525                 530 act gaa atg tgc atg agg aac att atc cag cag tta aag aat cag gtc              1929
Thr Glu Met Cys Met Arg Asn Ile Ile Gln Gln Leu Lys Asn Gln Val
                535                 540                 545 tta ttc ctt tta gat gac tac aaa gaa ata tgt tca atc cct caa gtc              1977
Leu Phe Leu Leu Asp Asp Tyr Lys Glu Ile Cys Ser Ile Pro Gln Val
                550                 555                 560 ata gga aaa ctg att caa aaa aac cac tta tcc cgg acc tgc cta ttg              2025
Ile Gly Lys Leu Ile Gln Lys Asn His Leu Ser Arg Thr Cys Leu Leu
                565                 570                 575 att gct gtc cgt aca aac agg gcc agg gac atc cgc cga tac cta gag              2073
Ile Ala Val Arg Thr Asn Arg Ala Arg Asp Ile Arg Arg Tyr Leu Glu
                580                 585                 590 acc att cta gag atc aaa gca ttt ccc ttt tat aat act gtc tgt ata              2121
Thr Ile Leu Glu Ile Lys Ala Phe Pro Phe Tyr Asn Thr Val Cys Ile
595                 600                 605                 610 tta cgg aag ctc ttt tca cat aat atg act cgt ctg cga aag ttt atg              2169
Leu Arg Lys Leu Phe Ser His Asn Met Thr Arg Leu Arg Lys Phe Met
                615                 620                 625 gtt tac ttt gga aag aac caa agt ttg cag aag ata cag aaa act cct              2217
Val Tyr Phe Gly Lys Asn Gln Ser Leu Gln Lys Ile Gln Lys Thr Pro
                630                 635                 640 ctc ttt gtg gcg gcg atc tgt gct cat tgg ttt cag tat cct ttt gac              2265
Leu Phe Val Ala Ala Ile Cys Ala His Trp Phe Gln Tyr Pro Phe Asp
                645                 650                 655 cca tcc ttt gat gat gtg gct gtt ttc aag tcc tat atg gaa cgc ctt              2313
Pro Ser Phe Asp Asp Val Ala Val Phe Lys Ser Tyr Met Glu Arg Leu
                660                 665                 670 tcc tta agg aac aaa gcg aca gct gaa att ctc aaa gca act gtg tcc              2361
Ser Leu Arg Asn Lys Ala Thr Ala Glu Ile Leu Lys Ala Thr Val Ser
675                 680                 685                 690 tcc tgt ggt gag ctg gcc ttg aaa ggg ttt ttt tca tgt tgc ttt gag              2409
Ser Cys Gly Glu Leu Ala Leu Lys Gly Phe Phe Ser Cys Cys Phe Glu
                695                 700                 705 ttt aat gat gat gat ctc gca gaa gca ggg gtt gat gaa gat gaa gat              2457
Phe Asn Asp Asp Asp Leu Ala Glu Ala Gly Val Asp Glu Asp Glu Asp
                710                 715                 720 cta acc atg tgc ttg atg agc aaa ttt aca gcc cag aga cta aga cca              2505
Leu Thr Met Cys Leu Met Ser Lys Phe Thr Ala Gln Arg Leu Arg Pro
                725                 730                 735 ttc tac cgg ttt tta agt cct gcc ttc caa gaa ttt ctt gcg ggg atg              2553
Phe Tyr Arg Phe Leu Ser Pro Ala Phe Gln Glu Phe Leu Ala Gly Met
                740                 745                 750 agg ctg att gaa ctc ctg gat tca gat agg cag gaa cat caa gat ttg              2601
Arg Leu Ile Glu Leu Leu Asp Ser Asp Arg Gln Glu His Gln Asp Leu
755                 760                 765                 770
```

```
gga ctg tat cat ttg aaa caa atc aac tca ccc atg atg act gta agc    2649
Gly Leu Tyr His Leu Lys Gln Ile Asn Ser Pro Met Met Thr Val Ser
            775                 780                 785 gcc tac aac aat ttt ttg aac tat gtc tcc agc ctc cct tca aca aaa    2697
Ala Tyr Asn Asn Phe Leu Asn Tyr Val Ser Ser Leu Pro Ser Thr Lys
            790                 795                 800 gca ggg ccc aaa att gtg tct cat ttg ctc cat tta gtg gat aac aaa    2745
Ala Gly Pro Lys Ile Val Ser His Leu Leu His Leu Val Asp Asn Lys
            805                 810                 815 gag tca ttg gag aat ata tct gaa aat gat gac tac tta aag cac cag    2793
Glu Ser Leu Glu Asn Ile Ser Glu Asn Asp Asp Tyr Leu Lys His Gln
820                 825                 830 cca gaa att tca ctg cag atg cag tta ctt agg gga ttg tgg caa att    2841
Pro Glu Ile Ser Leu Gln Met Gln Leu Leu Arg Gly Leu Trp Gln Ile
835                 840                 845                 850 tgt cca caa gct tac ttt tca atg gtt tca gaa cat tta ctg gtt ctt    2889
Cys Pro Gln Ala Tyr Phe Ser Met Val Ser Glu His Leu Leu Val Leu
            855                 860                 865 gcc ctg aaa act gct tat caa agc aac act gtt gct gcg tgt tct cca    2937
Ala Leu Lys Thr Ala Tyr Gln Ser Asn Thr Val Ala Ala Cys Ser Pro
            870                 875                 880 ttt gtt ttg caa ttc ctt caa ggg aga aca ctg act ttg ggt gcg ctt    2985
Phe Val Leu Gln Phe Leu Gln Gly Arg Thr Leu Thr Leu Gly Ala Leu
            885                 890                 895 aac tta cag tac ttt ttc gac cac cca gaa agc ttg tca ttg ttg agg    3033
Asn Leu Gln Tyr Phe Phe Asp His Pro Glu Ser Leu Ser Leu Leu Arg
900                 905                 910 agc atc cac ttc cca ata cga gga aat aag aca tca ccc aga gca cat    3081
Ser Ile His Phe Pro Ile Arg Gly Asn Lys Thr Ser Pro Arg Ala His
915                 920                 925                 930 ttt tca gtt ctg gaa aca tgt ttt gac aaa tca cag gtg cca act ata    3129
Phe Ser Val Leu Glu Thr Cys Phe Asp Lys Ser Gln Val Pro Thr Ile
            935                 940                 945 gat cag gac tat gct tct gcc ttt gaa cct atg aat gaa tgg gag cga    3177
Asp Gln Asp Tyr Ala Ser Ala Phe Glu Pro Met Asn Glu Trp Glu Arg
            950                 955                 960 aat tta gct gaa aaa gag gat aat gta aag agc tat atg gat atg cag    3225
Asn Leu Ala Glu Lys Glu Asp Asn Val Lys Ser Tyr Met Asp Met Gln
            965                 970                 975 cgc agg gca tca cca gac ctt agt act ggc tat tgg aaa ctt tct cca    3273
Arg Arg Ala Ser Pro Asp Leu Ser Thr Gly Tyr Trp Lys Leu Ser Pro
980                 985                 990 aag cag tac aag att ccc tgt cta gaa gtc gat gtg aat gat att gat    3321
Lys Gln Tyr Lys Ile Pro Cys Leu Glu Val Asp Val Asn Asp Ile Asp
995                 1000                1005                1010 gtt gta ggc cag gat atg ctt gag att cta atg aca gtt ttc tca gct    3369
Val Val Gly Gln Asp Met Leu Glu Ile Leu Met Thr Val Phe Ser Ala
                1015                1020                1025 tca cag cgc atc gaa ctc cat tta aac cac agc aga ggc ttt ata gaa    3417
Ser Gln Arg Ile Glu Leu His Leu Asn His Ser Arg Gly Phe Ile Glu
            1030                1035                1040 agc atc cgc cca gct ctt gag ctg tct aag gcc tct gtc acc aag tgc    3465
Ser Ile Arg Pro Ala Leu Glu Leu Ser Lys Ala Ser Val Thr Lys Cys
        1045                1050                1055 tcc ata agc aag ttg gaa ctc agc gca gcc gaa cag gaa ctg ctt ctc    3513
Ser Ile Ser Lys Leu Glu Leu Ser Ala Ala Glu Gln Glu Leu Leu Leu
    1060                1065                1070 acc ctg cct tcc ctg gaa tct ctt gaa gtc tca ggg aca atc cag tca    3561
Thr Leu Pro Ser Leu Glu Ser Leu Glu Val Ser Gly Thr Ile Gln Ser
1075                1080                1085                1090
```

```
caa gac caa atc ttt cct aat ctg gat aag ttc ctg tgc ctg aaa gaa    3609
Gln Asp Gln Ile Phe Pro Asn Leu Asp Lys Phe Leu Cys Leu Lys Glu
            1095                1100                1105 ctg tct gtg gat ctg gag ggc aat ata aat gtt ttt tca gtc att cct    3657
Leu Ser Val Asp Leu Glu Gly Asn Ile Asn Val Phe Ser Val Ile Pro
1110                1115                1120 gaa gaa ttt cca aac ttc cac cat atg gag aaa tta ttg atc caa att    3705
Glu Glu Phe Pro Asn Phe His His Met Glu Lys Leu Leu Ile Gln Ile
        1125                1130                1135 tca gct gag tat gat cct tcc aaa cta gta aaa tta att caa aat tct    3753
Ser Ala Glu Tyr Asp Pro Ser Lys Leu Val Lys Leu Ile Gln Asn Ser
    1140                1145                1150 cca aac ctt cat gtt ttc cat ctg aag tgt aac ttc ttt tcg gat ttt    3801
Pro Asn Leu His Val Phe His Leu Lys Cys Asn Phe Phe Ser Asp Phe
1155                1160                1165                1170 ggg tct ctc atg act atg ctt gtt tcc tgt aag aaa ctc aca gaa att    3849
Gly Ser Leu Met Thr Met Leu Val Ser Cys Lys Lys Leu Thr Glu Ile
            1175                1180                1185 aag ttt tcg gat tca ttt ttt caa gcc gtc cca ttt gtt gcc agt ttg    3897
Lys Phe Ser Asp Ser Phe Phe Gln Ala Val Pro Phe Val Ala Ser Leu
        1190                1195                1200 cca aat ttt att tct ctg aag ata tta aat ctt gaa ggc cag caa ttt    3945
Pro Asn Phe Ile Ser Leu Lys Ile Leu Asn Leu Glu Gly Gln Gln Phe
    1205                1210                1215 cct gat gag gaa aca tca gaa aaa ttt gcc tac att tta ggt tct ctt    3993
Pro Asp Glu Glu Thr Ser Glu Lys Phe Ala Tyr Ile Leu Gly Ser Leu
1220                1225                1230 agt aac ctg gaa gaa ttg atc ctt cct act ggg gat gga att tat cga    4041
Ser Asn Leu Glu Glu Leu Ile Leu Pro Thr Gly Asp Gly Ile Tyr Arg
1235                1240                1245                1250 gtg gcc aaa ctg atc atc cag cag tgt cag cag ctt cat tgt ctc cga    4089
Val Ala Lys Leu Ile Ile Gln Gln Cys Gln Gln Leu His Cys Leu Arg
            1255                1260                1265 gtc ctc tca ttt ttc aag act ttg aat gat gac agc gtg gtg gaa att    4137
Val Leu Ser Phe Phe Lys Thr Leu Asn Asp Asp Ser Val Val Glu Ile
        1270                1275                1280 ggt gag cta gtg ttt cag ctt gca tgg aag cca gtg gta tag            4179
Gly Glu Leu Val Phe Gln Leu Ala Trp Lys Pro Val Val
    1285                1290                1295 ccaagctttc tgctgcaaca tgtctatgta acatttgcc cctctagaaa ttttcaaccc    4239
gcttcctcat tttcactatc atactgttcc ttctagtgtc cttctgtgga tttaggcgca    4299
ttctggtcag atttggaagt acaaaaaggt ctcccatttg tggatataca agccctcaaa    4359
tctgcgttct tgccacctgg tgttttagac acctggccac atactctcct aagtactcct    4419
ttttaaaact gaagatgaat atacacacag aaaagtacaa aaatcatgtg tactgctcac    4479
tgaattttat tttcttattt tcttcttttt ttttttttg agacagagtt tcgctcgtgt    4539
tgcccaggct ggagtacaat ggcacgatct cgggtcactg caaactctgc ctcctgggtt    4599
caagcgattc tcctgcctca gcctcccaag tagctaggat tacaggtgaa cgccaccaca    4659
cctggctaat tttgtatttt tagtaaacac agggtttcac catgttggcc aggctagtct    4719
cgaactcctg acctcaagtg agccacagtg cctggcctga ggaactgaga tttctgtcga    4779
gacctgaagg gagaatggcc caggcatagt tggtagagga ggaattgaga catcatttca    4839
aacagaggta atcacttgtg tcatagcctg gagttaaaga gaaccagata tatttgaaga    4899
acttggggga aaaaaaggaa tgtctggagc aagaggcagg agtgagttgt gagaagaaga    4959
```

-continued

```
ctggagagga aagtaaaagc ccaattggag aggctttgtc gggtgtgtta caagggctgg      5019
atctcatttt cttactgctc agcactgtta ttttacgtta tttaaaacag ctgggagcgg      5079
tggctcaagc ttgtaatccc agcactttgg gaggccgagg cggatggatc acgaggtcag      5139
gagatcgaga ccatcctggc taacatggtg aaaccccgtc tctactaaaa atacaaaaaa      5199
ttagccaggc gtgatggcgg gcacctgtag tcccagctac tcgggaggct gaggcaggag      5259
aatggtgtga acccgggagg tggagcttga agtgagccaa gatcatgcca ctgcactcca      5319
gcctgggcaa cagaacgaga ctccgtctca aaaaaaaaaa acaaaaa                    5366
```

<210> SEQ ID NO 5
<211> LENGTH: 31
<212> TYPE: DNA
<213> ORGANISM: Artificial Sequence
<220> FEATURE:
<223> OTHER INFORMATION: Artificial Sequence: Synthesized oligonucleotide

<400> SEQUENCE: 5
gaggaattcc tacattttag gttctcttag t                                     31

<210> SEQ ID NO 6
<211> LENGTH: 28
<212> TYPE: DNA
<213> ORGANISM: Artificial Sequence
<220> FEATURE:
<223> OTHER INFORMATION: Artificial Sequence: Synthesized oligonucleotide

<400> SEQUENCE: 6
gaggaattca atttccacca cgctgtca                                         28

<210> SEQ ID NO 7
<211> LENGTH: 20
<212> TYPE: DNA
<213> ORGANISM: Artificial Sequence
<220> FEATURE:
<223> OTHER INFORMATION: Artificial Sequence: Synthesized oligonucleotide

<400> SEQUENCE: 7
aattaaccct cactaaaggg                                                  20

<210> SEQ ID NO 8
<211> LENGTH: 24
<212> TYPE: DNA
<213> ORGANISM: Artificial Sequence
<220> FEATURE:
<223> OTHER INFORMATION: Artificial Sequence: Synthesized oligonucleotide

<400> SEQUENCE: 8
cattatgctg agtgtgatat cccg                                             24

APOPTOSIS INHIBITORY PROTEIN, GENE ENCODING THE PROTEIN AND CDNA THEREOF

This Application is a Continuation-In-Part application of Ser. No. 09/239,797, filed Jan. 29, 1999, now abandoned, the teachings of which are hereby incorporated by reference.

BACKGROUND OF THE INVENTION

1. Field of the Invention

The present invention relates to a human apoptosis inhibitory protein, and a gene encoding the protein and the cDNA thereof. More specifically, the present invention relates to the genetic materials which are useful for the elucidation of the onset mechanism of various apoptic diseases such as human spinal muscular atropy, the diagnosis of the risk of the onset thereof, and the prevention of the onset thereof. In addition, the materials are useful for the development of clinical techniques and pharmaceutical agents for the amelioration and therapeutic treatment of the diseases.

2. Description of the Related Art

Apoptosis is a programmed cellular death, involving observed phenomena such as the loss of cellular contact with surrounding cells, cytoplasmic condensation, chromatin condensation and nuclear condensation with relation to endonuclease activity, nuclear fragmentation, membrane-enveloped spherical microbodies, the phagocytosis of spherical microbodies with adjacent macrophages or epithelial cells, or the fragmentation of the DNA nucleosome unit into DNAs of 180 to 200 bp due to endonuclease activity. It is suggested that apoptosis is a phagocytic mechanism for the final fragment of an apoptic somatic cell under such observed phenomena by adjacent cells (see for example Immunology Today 7: 115–119, 1986; Science 245:301–305, 1989).

As an apoptosis inhibitory gene, for example, gene bcl-2 has been known. The gene bcl-2, one of oncogenes discovered in 1985 in alveolar B cytoma, is highly expressed in the immune system and nervous system, and it is believed that the expression product of the gene serves to maintain the homeostasis of the human immune functions and neuronal functions, by inhibiting the apoptosis of the cells involved. Additionally because the bcl-2 is expressed in a diversified range in fetuses in particular, the gene is believed to play a significant role in morphological formation during ontogenesis.

Meanwhile, the present inventors have isolated the gene of a neuronal apoptosis inhibitory protein (NAIP) from the human chromosome 5q13.1 region as an etiological gene of a familial hereditary disease spinal muscular atropy (SMA) (Roy et al., Cell 80: 167–178, 1995), and have filed a patent application (PCT/CA95/00581). More specifically, it is supposed that the mutation of the NAIP gene or the decrease of the copy number thereof might cause the apoptosis of spinal neuron, which is an etiology of the SMA onset. It is apparently demonstrated that by introducing the NAIP gene into various cultured cells to give apoptosis-inducing stimulation to the cells, the death of the cells is inhibited (Liston et al., Nature 379: 349–353, 1996), which indicates that NAIP plays a role of an apoptosis inhibitory factor for not only neuronal cells but also overall somatic cells.

SUMMARY OF THE INVENTION

The present inventors have further promoted the analysis of the NAIP gene, and they have successfully achieved to clone the full length of cDNA of NAIP gene and to identify the protein encoded in the cDNA.

It is an object of the present invention to provide the cDNA of NAIP gene thus found by the present inventors, genetic materials with relation to the cDNA and the expression products thereof and the like in industrially applicable forms.

An invention provided by the present application is a human apoptosis inhibitory protein which comprises the amino acid sequence of SQ ID No:1, or an amino acid sequence with deletion, substitution or addition of a single or plural amino acids in SQ ID No:1.

Another invention is a human apoptosis inhibitory protein comprising the amino acid sequence of SQ ID No:3, or an amino acid sequence with deletion, substitution or addition of a single or plural amino acids in SQ ID No:3.

Other inventions are a human gene encoding the human apoptosis inhibitory proteins, cDNAs of said human gene which comprises at least the nucleotide sequence for the coding region of SQ ID No:2 or NO:4.

Still additionally, inventions of this application are an antibody against the human apoptosis inhibitory proteins, a non-human animal gene to which the above cDNAs are hybridized, recombinant vector carrying the cDNAs or a partial sequence thereof, a DNA probe comprising a partial sequence of the cDNAs, and a set of PCR primer corresponding to partial sequences of the cDNAs.

The present inventions will now be described below in more detail with reference to embodiments.

DESCRIPTION OF THE PREFERRED EMBODIMENTS

Figure 1:
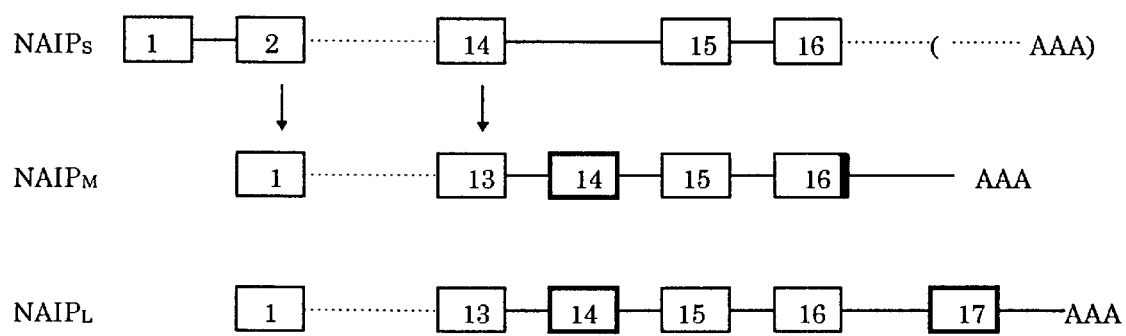
FIG. 1 schematically depicts the individual 3'-terminal structures of the conventionally known apoptosis inhibitory gene $NAIP_S$ and the inventive genes $NAIP_M$ and $NAIP_L$.

The human apoptosis inhibitory protein of the present invention is a human protein comprising the amino acid sequence of SQ ID No.1 or 3. A peptide (with 5 amino acid residues or more) consisting of any partial amino acid sequence of the amino acid sequence of SQ ID No.1 or 3 is included in the scope of this protein. Such peptide may be used as an antigen to prepare an antibody, for example. Furthermore, the protein of the present invention includes fusion proteins with other proteins (for example, fluorescent proteins).

According to known methods, the protein of the present invention may be isolated from human organs or cell lines. When intending to use the protein as a peptide, the protein may be prepared on the basis of the amino acid sequences provided by the present invention by chemical synthesis. Otherwise, the protein may be obtained through in vitro transcription or a recombinant DNA technique by using a cDNA fragment provided by the present invention. In order to obtain the protein by the recombinant DNA technique, for example, the protein of the present invention may be expressed at a large scale from a host cell (*Escherichia coli, Bacillus subtilis*, yeast, animal or plant cells, etc.) which has been transformed by a recombinant vector prepared by inserting the cDNA fragment of the present invention in an appropriate expression vector. For expressing the protein in a microorganism such as *Eschertchia coli*, more specifically, the cDNA of the present invention is inserted within an expression vector having an origin suitable for the microorganism, a promoter sequence, a ribosome-binding site, DNA cloning sites, a terminator sequence and the like to prepare an expression vector, which is used to transform a host cell and thereafter culture the resulting transformant, whereby a protein encoded by the cDNA can be produced in the microorganism at a large scale. Otherwise, the protein may be expressed in the form of a fused protein with other proteins. By hydrolyzing the resulting fused protein with an appropriate protease, a protein part encoded by the cDNA may be recovered. For intending to allow the protein of the present invention to be expressed and secreted in an animal cell, alternatively, the cDNA fragment is inserted within an animal cell expression vector with an animal cell promoter, a splicing region, a poly(A) additional site, and the like, the protein of the present invention may be expressed in the animal cell.

The gene of the present invention is derived from humans and other mammals and encodes the protein, and can be isolated from the known genomic libraries by using the cDNA of the present invention or a partial sequence thereof as the probe.

The cDNA of the present invention comprises the nucleotide sequence of SQ ID No.2 or 4. The cDNAs of the nucleotide sequences of SQ ID Nos.2 and 4 encode the proteins of the amino acid sequences of SQ ID Nos.1 and 3, respectively.

Because the protein of the present invention is expressed in any human tissue, a clone identical to the cDNA of the present invention may readily be recovered by screening human cDNA libraries by using an oligonucleotide probe synthesized on the basis of the nucleotide sequence of the cDNA of SQ ID No.2 or 4. Otherwise, the objective cDNA may be synthesized by polymerase chain reaction (PCR) by using such oligonucleotides as primers. Generally, it is frequently observed that human genes have polymorphism due to differences of individual nucleotide. Thus, cDNAs in which the addition and deletion of a single or plural nucleotides and/or the substitution with a single or plural nucleotides occur in SQ ID No.2 or 4 are also encompassed within the scope of the present invention. Similarly, proteins in which the addition and deletion of a single or plural amino acid residues and/or the substitution with a single or plural amino acid residues occur due to such modification are also encompassed within the scope of the present invention, as long as the proteins have the activities of the protein with the amino acid sequence of SQ ID No.1 or 3.

Additionally, the partial sequence of the cDNA of the present invention is a continuous sequence of 10 bp or more in the nucleotide sequence of SQ ID No.2 or 4, and DNA fragments (sense chain and antisense chain) comprising such continuous sequence are also encompassed within the scope of the present invention. These DNA fragments may be used as probes for genetic diagnosis, for example.

Furthermore, the antibody of the present invention may be prepared in the form of a polyclonal antibody or monoclonal antibody, by known methods by using the protein described above of itself or a partial peptide thereof as an antigen.

The present invention will now be described more specifically in more detail in examples, but the invention is not limited to the following examples.

EXAMPLES

Example 1

Screening of cDNA Library

Exxon 16 of the NAIP gene was PCR amplified by using the oligonucleotides of SQ ID Nos.5 and 6 as primers. PCR conditions were as follows; 94° C. for 15 seconds, 56° C. for 30 seconds and 72° C. for one minute.

By using the resulting PCR product, then, the cDNA library of human fetal brain (NA 937227; Stratagene) was screened. As a result, eight clones with overlaps with the NAIP gene were identified.

As a result of the sequence analysis, the eight cDNA clones were separated into seven clones having the same coding region at the 3' termini and one clone comprising a shorter DNA fragment than those of the seven clones. Based on the length of the DNA fragments, furthermore, it was identified that the genes encoding these clones were longer DNA molecules than the NAIP gene previously reported.

For convenience, hereinafter, the conventionally known NAIP gene is referred to as $NAIP_S$; the gene encoding the longer cDNA thus screened is referred to as $NAIP_L$; and the shorter gene is referred to as $NAIP_M$.

Example 2

Sequencing of the cDNAs

The nucleotide sequences of the cDNA clones identified in Example 1 were determined. By using the sequences determined by using the oligonucleotides of SQ ID Nos.7 and 8 as primary primers, additional primers were sequentially prepared, to determine the full sequences of the cDNAs by the walking method.

Consequently, it is confirmed that the conventionally known exons of $NAIP_S$ (upper column, FIG. 1) is inaccurate. $NAIP_M$ and $NAIP_L$ do not have exon 1 of $NAIP_S$ and have a new exon (153 bp) between the exons 14 and 15 of the $NAIP_S$ (middle and lower columns, FIG. 1). Additionally, it is confirmed that $NAIP_L$ have an additional exon at the 3' terminus of the $NAIP_M$ (lower columns, FIG. 1).

In other words, the NAIP is expressed in two splice variant forms, $NAIP_M$ with exons 1 to 16 and $NAIP_L$ with exons 1 to 17. In more detail, $NAIP_M$ has the novel exon 14 and additionally contains extra 39 bp at the 3' terminus of the exon 16, while the cDNA thereof has the nucleotide sequence of SQ ID No.4 and encodes the protein of the amino acid sequence of SQ ID No.3. On the other hand, $NAIP_L$ contains exon 17 of 363 bp in addition to the exon 14, while the cDNA thereof has the nucleotide sequence of SQ ID No.2 and encodes the protein of the amino acid sequence of SQ ID No.1.

Based on the aforementioned results, it is verified that the apoptosis inhibitory genes $NAIP_M$ and $NAIP_L$ of the present invention are novel genes, apparently different from the conventionally known gene $NAIP_S$; and that the apoptosis inhibitory proteins encoded by these genes are novel proteins.

Example 3

Expression of Protein in *Escherichia coli*

A translated region was PCR amplified by using an $NAIP_L$-containing clone isolated in Example 1 as template. The resulting PCR product was inserted into an expression vector for *Escherichia coli*, and after confirming the nucleotide sequence of the insert, the host *Escherichia coli* was transformed with the vector. The transformant was cultured in an LB culture medium at 37° C. for 5 hours, followed by addition of IPTG to a final concentration of 0.4 mM and subsequent additional culturing at 37° C. for 2.5 hours. The bacteria were centrifuged and isolated, and were then dissolved in a dissolving solution, and the resulting solution was once frozen at −80° C. and thawed, for ultrasonic disruption. The solution in disruption was centrifuged, and from the resulting supernatant was isolated and purified a protein, which was recovered as the apoptosis inhibitory protein (SQ ID No.1) of the present invention.

Example 4

Preparation of Antibody

A rabbit was immunized with the protein obtained in Example 3 as an antigen, to prepare an anti-serum. From the antiserum was first removed a 40%-saturated ammonium sulfate precipitate fraction on a GST affinity column. The pass-through fraction was further purified on an antigen column GST-HP10345.

As has been described above, the novel apoptosis inhibitory proteins, the gene encoding the proteins and the cDNAs thereof are provided in accordance with the present invention, whereby the elucidation of the onset mechanism of various apoptic diseases primarily including human spinal muscular atropy, the diagnosis of the risk of the onset thereof, the prevention of the onset thereof and the amelioration of the diseased conditions, and the development of clinical techniques and pharmaceutical

What is claimed is:

1. A polypeptide comprising the amino acid sequence of SEQ ID No.3.

2. The polypeptide according to claim 1, having an apoptosis inhibitory activity.

3. The polypeptide according to claim 1, which is a human protein.

4. The polypeptide according to claim 1, which consists of the amino acid sequence of SEQ ID No.3.

* * * * *